US009395240B2

United States Patent
Krufka

(10) Patent No.: US 9,395,240 B2
(45) Date of Patent: Jul. 19, 2016

(54) METHODS, SYSTEMS, AND APPARATUS FOR BIOLOGICAL SAMPLE ILLUMINATION AT MULTIPLE WAVELENGTHS

(75) Inventor: Frank Krufka, Kirkwood, PA (US)

(73) Assignee: SIEMENS HEALTHCARE DIAGNOSTICS INC., Tarrytown, NY (US)

( * ) Notice: Subject to any disclaimer, the term of this patent is extended or adjusted under 35 U.S.C. 154(b) by 227 days.

(21) Appl. No.: 14/114,598

(22) PCT Filed: May 3, 2012

(86) PCT No.: PCT/US2012/036246
§ 371 (c)(1),
(2), (4) Date: Oct. 29, 2013

(87) PCT Pub. No.: WO2012/151358
PCT Pub. Date: Nov. 8, 2012

(65) Prior Publication Data
US 2014/0203173 A1    Jul. 24, 2014

Related U.S. Application Data

(60) Provisional application No. 61/482,307, filed on May 4, 2011.

(51) Int. Cl.
*G01J 1/42* (2006.01)
*G01J 3/10* (2006.01)
(Continued)

(52) U.S. Cl.
CPC .... *G01J 1/42* (2013.01); *G01J 3/10* (2013.01); *G01J 3/42* (2013.01); *G01N 21/645* (2013.01);
(Continued)

(58) Field of Classification Search
CPC ................ G01J 1/42; G01J 3/10; G01J 3/42; G01N 2021/6419; G01N 2021/6421; G01N 2021/6478; G01N 21/645; G01N 21/6452; G01N 2201/0627
See application file for complete search history.

(56) References Cited

U.S. PATENT DOCUMENTS

2001/0019405 A1    9/2001    Herron et al.
2004/0038390 A1    2/2004    Boege et al.
(Continued)

FOREIGN PATENT DOCUMENTS

CN    101776599    7/2010
FR    2928220      9/2009
(Continued)

OTHER PUBLICATIONS

International Search Report dated Aug. 7, 2012, International Application No. PCT/US2012/36246.
(Continued)

*Primary Examiner* — Francis M Legasse, Jr.
(74) *Attorney, Agent, or Firm* — Dugan & Dugan, PC

(57) ABSTRACT

Disclosed are methods and apparatus adapted to aid in an illumination of a test sample in a test vessel. The method includes sequencing multiple wavelength light sources by turning OFF all but the light source of interest and taking a reading. The illumination apparatus has a bracket with a first and second arms and a space between them adapted to receive a test vessel, an array of light sources and a lens array coupled to the first arm, an array of bandpass filters adapted to filter light signals from each light source, at least one aperture array adapted to limit an extent of light emitted to the test vessel, and a single photo detector coupled to the second arm adapted to receive light signals from each of the light sources without moving the test vessel. Systems are disclosed, as are other aspects.

20 Claims, 10 Drawing Sheets

(51) Int. Cl.
  *G01J 3/42* (2006.01)
  *G01N 21/64* (2006.01)

(52) U.S. Cl.
  CPC .... *G01N 21/6452* (2013.01); *G01N 2021/6419* (2013.01); *G01N 2021/6421* (2013.01); *G01N 2021/6478* (2013.01); *G01N 2201/0627* (2013.01)

(56) References Cited

U.S. PATENT DOCUMENTS

2006/0274313 A1 12/2006 Gilbert et al.
2007/0098595 A1 5/2007 Tam et al.
2010/0014068 A1 1/2010 Padmanabhan et al.
2010/0065726 A1* 3/2010 Zhong et al. ............. 250/227.24
2010/0157302 A1 6/2010 Serai et al.

FOREIGN PATENT DOCUMENTS

JP H06201468 7/1994
JP 2000-258341 9/2000

OTHER PUBLICATIONS

European Search Report of European Application No. 12779855.1 dated Dec. 10, 2014.

* cited by examiner

METHODS, SYSTEMS, AND APPARATUS FOR BIOLOGICAL SAMPLE ILLUMINATION AT MULTIPLE WAVELENGTHS

FIELD OF THE INVENTION

The present invention relates generally to methods, systems and apparatus adapted to illuminate biological fluid samples.

BACKGROUND OF THE INVENTION

In medical testing, the detection of photoluminescence or absorbance may be used as a mechanism to determine a characteristic of a sample of a biological fluid (otherwise referred to as "specimens" or "samples"). For example, in some automated testing systems (e.g., clinical analyzers) reaction vessels, such as cuvettes, flow through vessels, sample cups, vials, and the like, may receive samples (e.g., plasma) possibly containing one or more reagents (referred to herein as a "test sample"). The test sample in the test vessel may be provided in an illumination assembly. A light source may be projected through the test sample, and the light emanating from the test sample is detected by a photodetector. However, such systems may require the use of a reference detector to enable obtaining a reference value. Moreover, such systems may suffer from instability during use due to temperature variations of the light source.

Accordingly, methods, systems and apparatus that may improve accuracy and simplicity of illumination systems in clinical testing are desired.

SUMMARY OF THE INVENTION

In a method aspect, an improved method of illuminating a test sample is provided. The method includes providing an illumination apparatus having a plurality of controllable light sources, each having an emission center wavelength; providing a test vessel containing the test sample; providing a constant current to each of the plurality of controllable light sources; turning off all but a single one of the plurality of controllable light sources; receiving a changed light signal at a single detector from the single one light source passed through the test sample; and repeatedly turning off all but a single other light source until readings at all wavelength bands of interest are obtained.

In an apparatus aspect, an improved sample illumination apparatus is provided. The illumination apparatus includes a bracket including a first arm and a second arm and a space between the arms adapted to receive a test vessel; an array of light sources coupled to the first arm; a lens array coupled to the first arm, a lens aligned with each light source in the array of light sources in a direction of light signal travel towards the space; an array of bandpass filters, a bandpass filter aligned with each light source; at least one aperture array; and a single photo detector coupled to the second arm.

According to another aspect, an improved sample illumination system is provided. The illumination system includes a bracket including a first arm and a second arm and a space between the arms; a test vessel provided in the space; an array of light sources operable to provide light signals through the test vessel; an array of lenses, a lens corresponding to each light source; an array of bandpass filters adapted to filter the light signals from the array of light sources, a filter corresponding to each light source; at least one aperture array; a single detector adapted to receive changed light signals passing through the test vessel; and a controller operable to control a sequence of light signals emitted from the array of light sources.

Still other aspects, features, and advantages of the present invention may be readily apparent from the following detailed description by illustrating a number of exemplary embodiments and implementations, including the best mode contemplated for carrying out the present invention. The present invention may also be capable of other and different embodiments, and its several details may be modified in various respects, all without departing from the spirit and scope of the present invention. Accordingly, the drawings and descriptions are to be regarded as illustrative in nature, and not as restrictive. The drawings are not necessarily drawn to scale. The invention is to cover all modifications, equivalents, and alternatives falling within the spirit and scope of the invention.

DETAILED DESCRIPTION

As discussed above, in automated clinical analyzers, achieving precision and simplicity in the illumination of test samples is desirable. In particular, because light sources tend to be relatively temperature sensitive, variations in intensity over time may affect testing results. Accordingly, means for precisely illuminating a sample at multiple wavelengths is desired. Moreover, reducing the number of expensive sensors is also desirable, especially reducing the need for a separate reference sensor.

In view of the foregoing problems, the present invention provides methods, systems, and apparatus adapted to illuminate a test sample contained in a test vessel.

In a first aspect, a method of illumination of a test sample is provided. According to the method, a plurality of light sources having predefined emission center wavelengths are provided. Initially, all the light sources may be driven with generally constant current until stable temperature and intensity output is achieved. Then, one by one, readings are taken at the individual wavelengths by turning off all but the light source of interest and receiving the light signal at a common detector. In this way, readings at the multiple wavelengths may be rapidly obtained. A baseline reading may be obtained using the same detector, but without a test sample. In some embodiments, the light sources, detector and test vessel may be aligned so that each reading at each wavelength may be sequentially taken without moving the test vessel. In other embodiments, the test vessel may be moved relative to each light source and a reading taken.

In another aspect, an illumination apparatus and system is provided. The illumination apparatus includes a bracket with a first and second arms and a space between them adapted to receive a test vessel; an array of light sources and a lens array coupled to the first arm; an array of bandpass filters adapted to filter light signals from each light source, at least one aperture array adapted to limit an extent of light emitted to the test vessel; and a single photo detector coupled to the second arm adapted to receive light signals from each of the light sources.

These and other aspects and features of the invention will be described with reference to FIGS. 1A-7 herein.

Figure 1A:
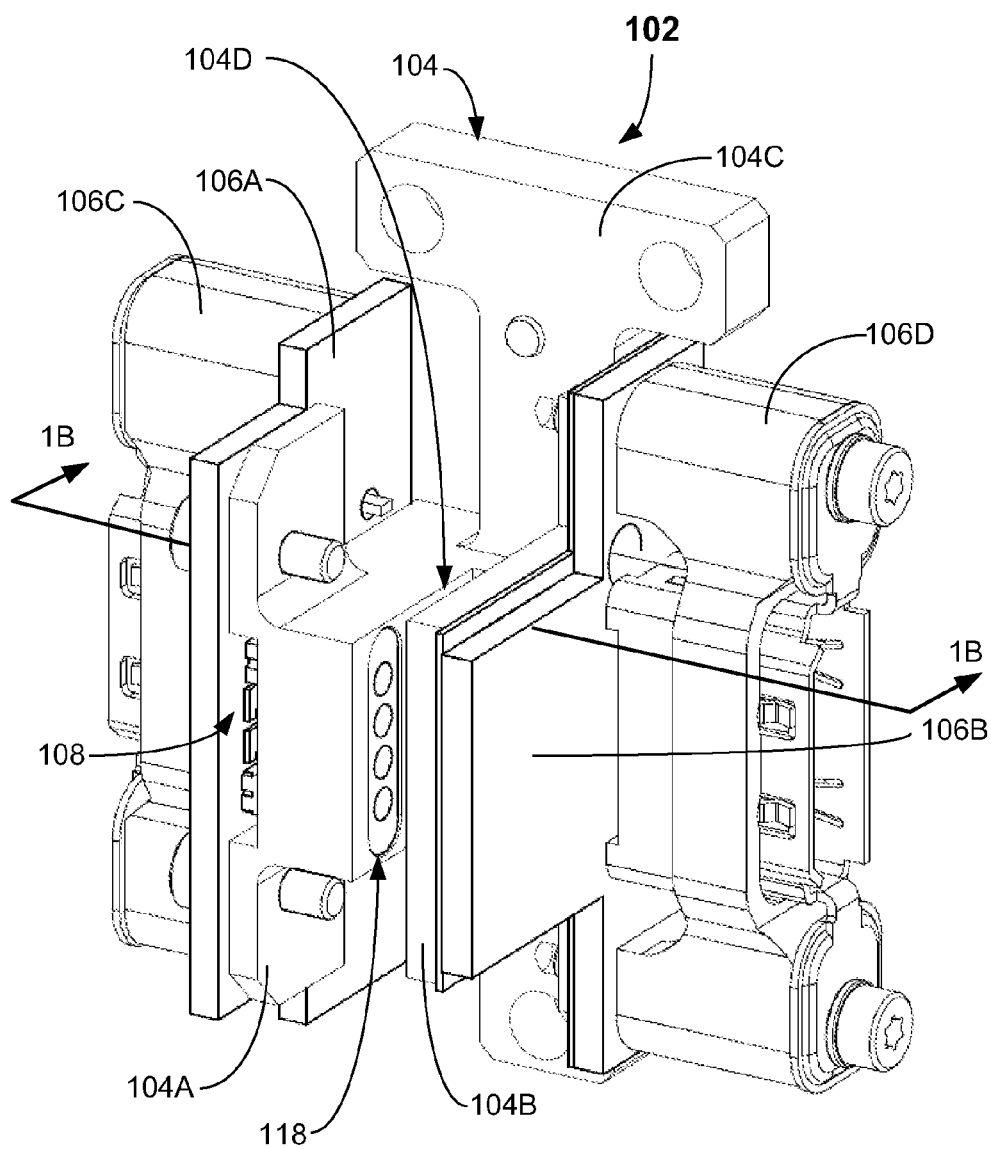
FIG. 1A is an isometric view illustration of an exemplary illumination apparatus according to embodiments of the invention.
Figure 1B:
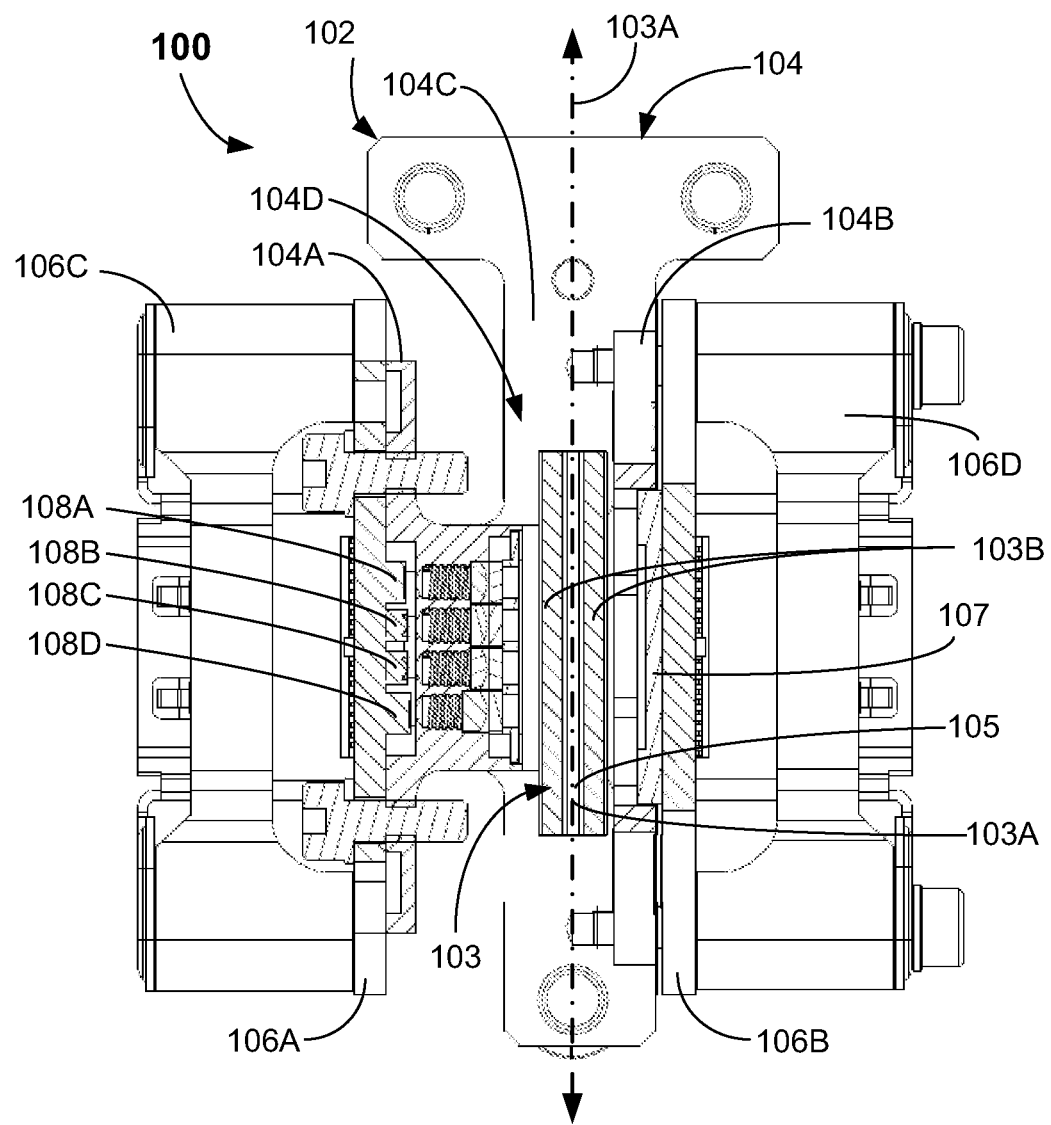
FIG. 1B is a cross sectioned side view illustration of the exemplary illumination apparatus of FIG. 1A taken along section line 1B-1B and showing a flow through test vessel according to embodiments of the invention.
Figure 1C:
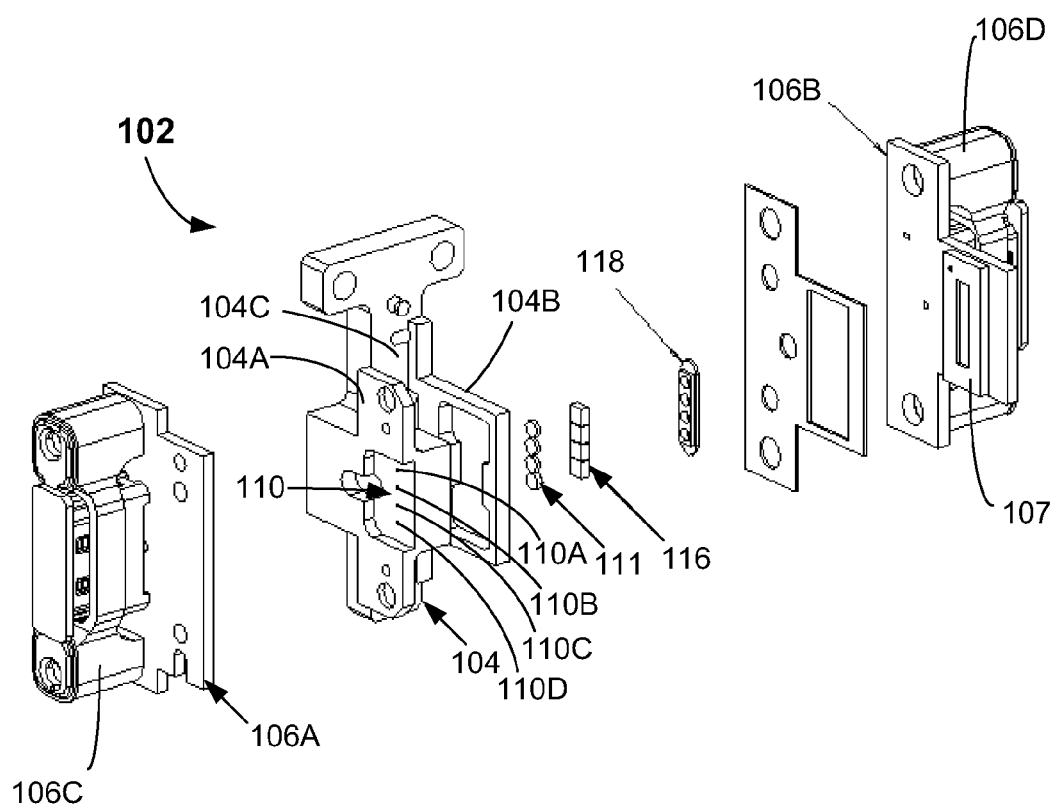
FIG. 1C is an exploded view illustration of component parts of an exemplary illumination apparatus according to embodiments of the invention.

In accordance with a first embodiment of the invention, as best shown in FIGS. 1A-1E, an illumination system 100 including an illumination apparatus 102 and a test vessel 103 is shown. The illumination apparatus 102 is useful and operable to illuminate a test sample 105 contained in the test vessel 103 (e.g., a cuvette or a sample flow through passage). Any suitable configuration of test vessel 103 adapted to contain a test sample 105 to be illuminated may be used. The biological sample provided in the sample illumination system 100 may have been aspirated from a sample container 208 contained or held in a sample rack 210, for example, as shown in FIG. 2. In some embodiments, a reagent from a reagent container (not shown) may be added to the biological sample contained in the test vessel 103 to form a test sample 105 and promote a reaction with an analyte or other material in the biological sample. However, it should be apparent that the present invention may be used to illuminate test samples that do not contain a reagent as well.

Figure 1D:
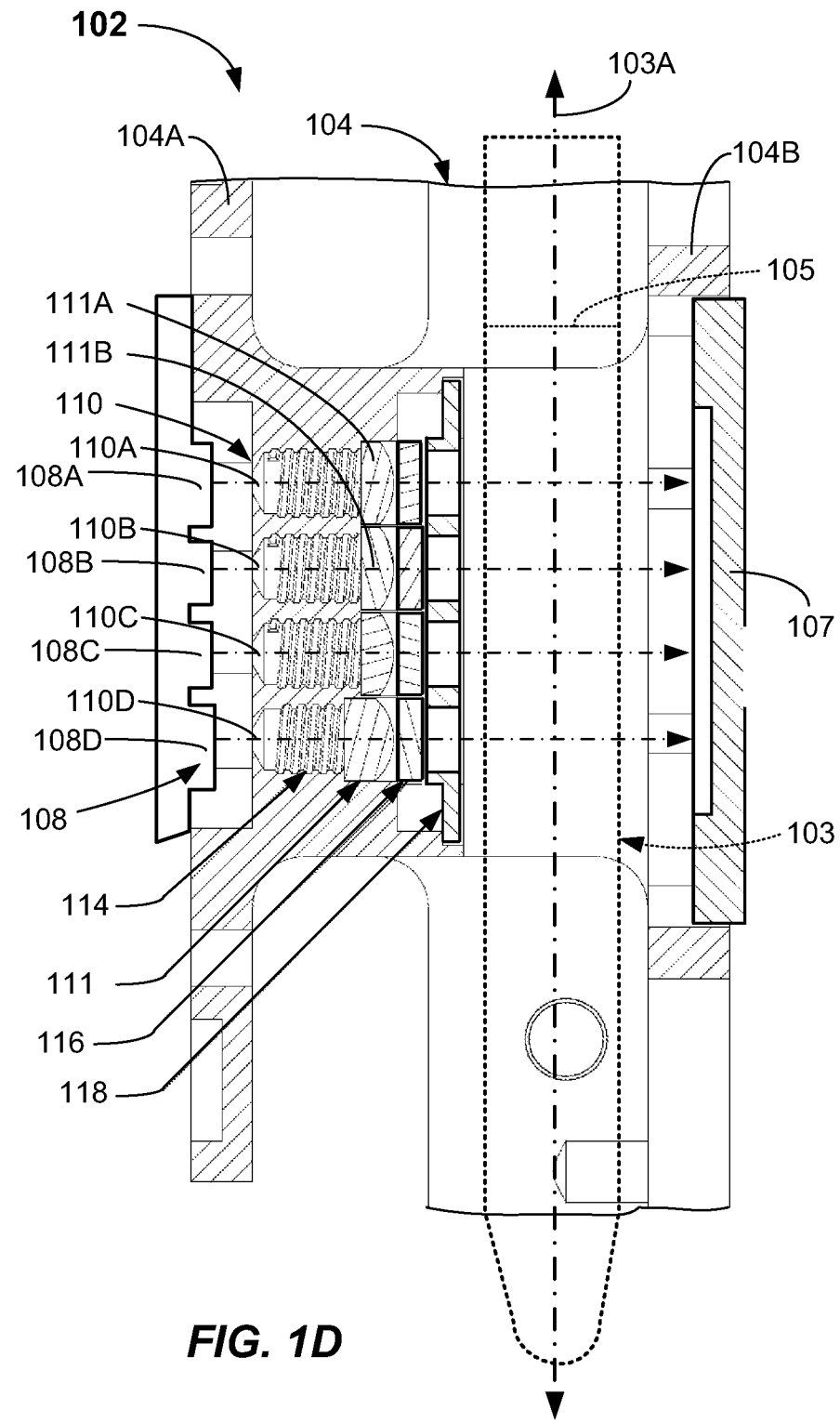
FIG. 1D is an enlarged partial cross sectioned illustration of several component parts of an illumination apparatus according to embodiments of the invention.
Figure 2:
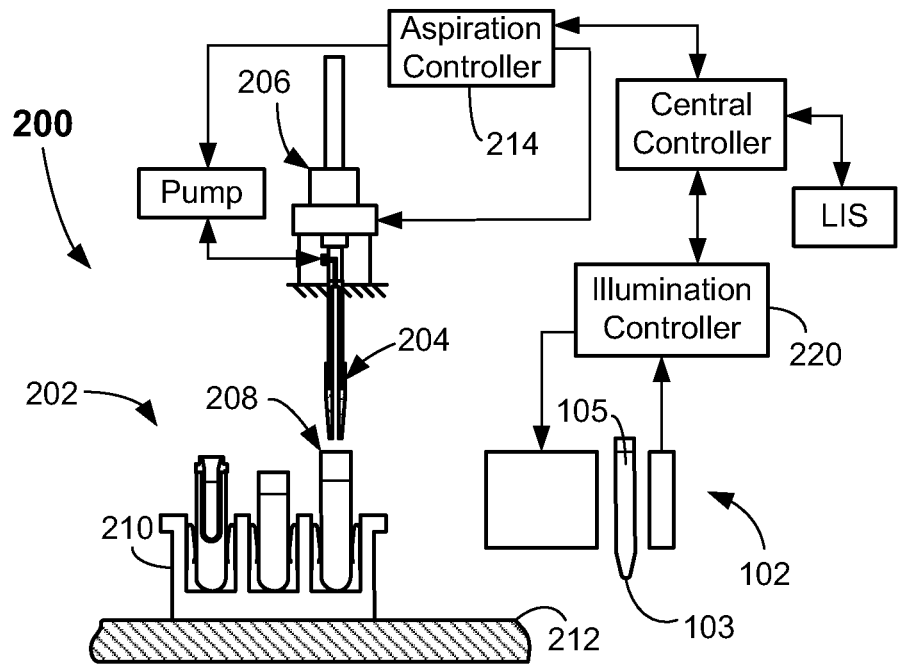
FIG. 2 is a side view graphical depiction of a clinical analyzer including an illumination apparatus according to embodiments of the invention.
Figure 3:
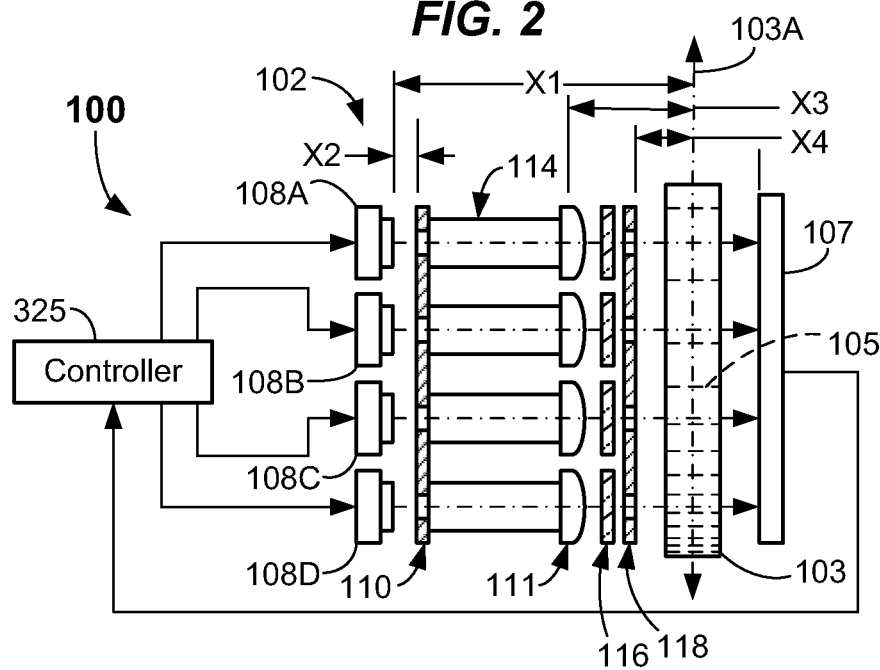
FIG. 3 is a side view graphical illustration depicting a collection of component parts in an illumination system according to embodiments of the invention.

As shown in FIGS. 1D and 2, the test vessel 103 may be a cuvette containing the test sample 105. In FIG. 1B, the test vessel 103 may include a flow-through passage 103A. The flow-through passage 103A may be a slender channel having transparent side walls 103B that extend along the length of the flow-through passage 103A.

As shown in FIG. 1B, an illumination system 100 may include the flow-through passage 103A provided in a space 104D and the test sample 105 therein may be illuminated by the illumination apparatus 102. The flow-through test vessel assembly 103 is positioned between the first and second arms 104A, 104B of the previously-described illumination system 100 at a defined location. The flow-through test vessel 103 may be received and positioned relative (e.g., by brackets or other locating means) to the illumination apparatus 102 in close proximity to register and locate the test vessel 103 relative to the illumination apparatus 102.

The flow-through passage 103A may extend from the first end to the second end and may include planar sidewalls 103B on either side of the passage 103A of about 1 mm thick and about 2 mm wide of a transparent material such as glass, or highly transparent acrylic plastic such as a polymethyl methacrylate plastic. Other transparent materials may be used. The flow through passage 103A at the portion that is illuminated by the illumination apparatus 102 may be about 18 mm long by about 2 mm wide and about 1 mm thick (normal to the direction of light passage). The test vessel 103 (shown terminated) may fluidly couple to one or more test sample delivery components (not shown) of the clinical analyzer 200 (FIG. 2). In operation, a test sample 105 is provided in the flow-through passage 103 and illuminated in the passage wherein the passing light signals that have passed through the test vessel 103 and test sample 105 are then received at a detector 107.

Again referring to FIGS. 1A-1E and FIG. 2, the illumination apparatus 102 may be included in a clinical analyzer 200 (FIG. 2) at any suitable location. The illumination apparatus 102 may include a bracket 104 adapted to rigidly mount the apparatus 102 in a fixed orientation to a frame (not shown) of the clinical analyzer 200. The bracket 104 may include a first arm 104A and a second arm 104B spaced from the first arm 104A, and a connecting portion 104C that is adapted to be secured to the frame by suitable fasteners or the like. The arms 104A, 104B may extend from the connecting portion 104C so as to form a U-shaped configuration. Opposed facing surfaces of the arms 104A, 104B may include generally planar parallel surfaces. The bracket 104 including the first arm 104A and second arm 104B may include a space 104D between the arms 104A, 104B configured and adapted to receive the test vessel 103.

Figure 4:
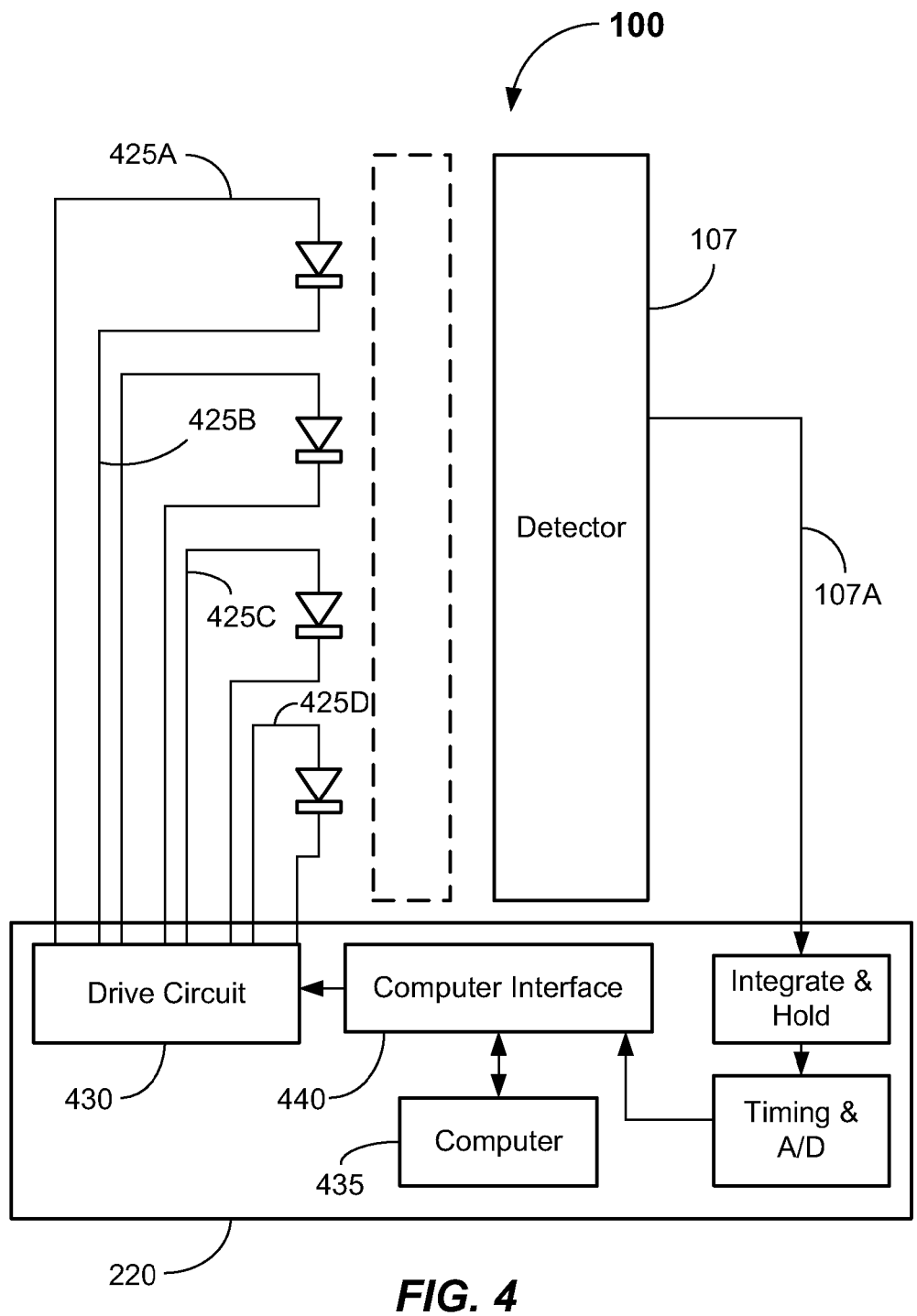
FIG. 4 is a side view graphical illustration depicting controller components of an illumination system according to embodiments of the invention.
Figure 5:
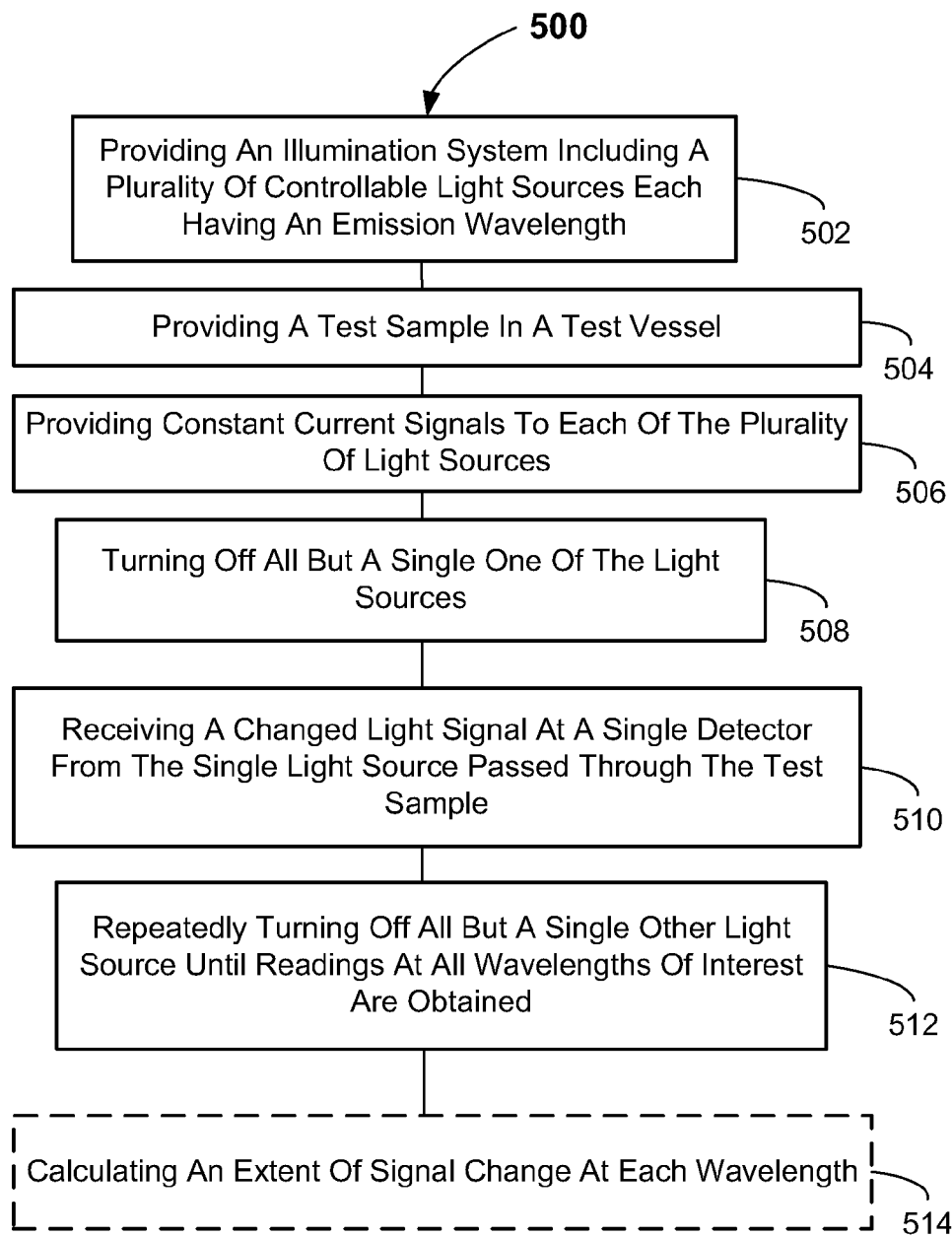
FIG. 5 is a flowchart illustrating a method according to embodiments of the present invention.

Mounted to the bracket 104 may be first and second circuit boards 106A, 106B. First circuit board 106A may include circuitry and a light array 108 containing a plurality of light sources (e.g., four light sources 108A-108D) mounted thereon or otherwise connected thereto, such as light emitting diodes (LEDs) (FIG. 1B). Surface mount LEDs may be used, such as Model # APTL3216 light emitting diodes from Kingbright Corporation of City of Industry, Calif. may be used. A drive circuit 430 (FIG. 4) may also be provided on the circuit board 106A. The second circuit board 106B may be composed of a single detector 107 configured and adapted to receive the light signals emitted from the light sources 108A-108D (e.g., LEDs), as will be described more fully below. Electronics adapted to carry out integration, hold, timing, and A/D functions may also be provided on the second circuit board 106B (See FIG. 4). Electrical connectors 106C, 106D allow the connection of the illumination apparatus 102 to a computer 435 (FIG. 4). The computer 435 may control a routine that sends a sequence of drive signals to the drive circuit 430 and also processes the received signals from the detector 107 to determine the degree of absorption, emission, fluorescence, chemiluminescence, or combinations thereof at the various wavelengths.

The light sources 108A-108D (e.g., LEDs) may each have an emission wavelength centered at a different center wavelength (e.g., four separate center wavelengths). Other numbers of wavelengths and light sources may be used. For example, the first light source 108A may include a center wavelength of about 365 nm. The second light source 108A may include a center wavelength of about 415 nm. The third light source 108A may include a center wavelength of about 470 nm. The fourth light source 108A may include a center wavelength of about 645 nm. Other center wavelengths may be used. The light sources 108A-108D (e.g., LEDs) in the depicted embodiment may be aligned (e.g., vertically) along a common axis that is parallel with a center axial axis 103A of the test vessel 103, and each may be spaced generally equidistant from the center axial axis 103A of the test vessel 103. The spacing X1 (FIG. 3) of the light sources 108A-108D (e.g., LEDs) from the center axial axis 103A may be about 7.80 mm. Other spacing dimensions may be used. The spacing of the light sources 108A-108D along the center axial axis 103A should be as compact as possible such that all the light sources may project onto the common detector 107 in the depicted embodiment without moving the test vessel 103.

Figure 1E:
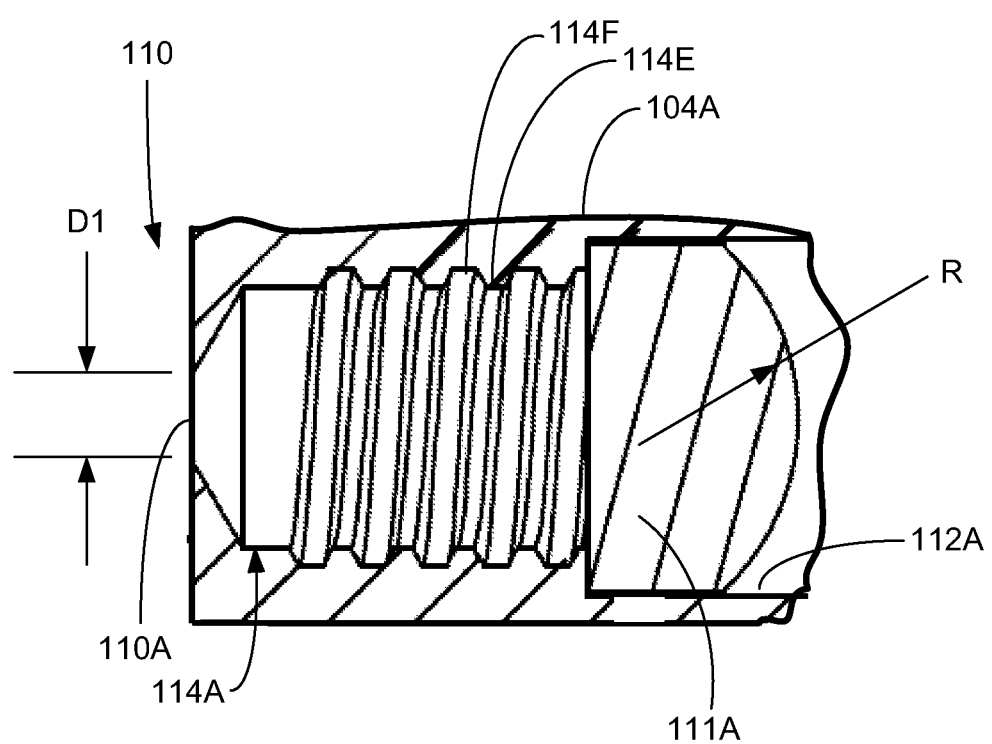
FIG. 1E is an enlarged partial cross sectioned illustration of a lens assembly of the illumination apparatus of FIG. 1D according to embodiments of the invention.

Now referring to FIGS. 1C-1E and FIG. 3, immediately following the plurality of light sources 108A-108D (e.g., LEDs) is a first aperture array 110. An enlarged view of an individual aperture 110A of the aperture array 110 is shown in FIG. 1E. The first aperture array 110 is configured, functions, and is adapted to allow each of the light signals (shown as dotted arrows in FIGS. 1D and 3) from the light sources 108A-108D (e.g., LEDs) to pass through the first aperture array 110, but also limit an extent of the light passing through the aperture array 110, such that the light signals are confined to a direction towards the test vessel 103 and detector 107. The first aperture array 110 may limit an extent of the light passing to a lens array 111 that is positioned on an opposite side of the first aperture array 110 from the light sources 108A-108D (e.g., LEDs). Each of the apertures 110A-110D in the aperture array 110 may be circular in shape, and each may have a diameter (D1) as shown in FIG. 1E of between about 0.35 mm and about 0.65 mm. Each aperture 110A-110D may have a nominal diameter of about 0.5 mm, for example. The aperture array 110 may be formed as through holes in the first portion 104A of the bracket 104, for example. Optionally, it should be understood that the apertures 110A-110D of the aperture array 110 may be formed in a separate member that is mounted in a fixed spatial relationship to the light sources 108A-108D (e.g., LEDs). The apertures 110A-110D may be generally aligned axially and centered relative to the faces of light sources 108A-108D (e.g., LEDs). The openings of the aperture array 110 may be generally spaced a distance X2 of about 0.250 mm from the front faces of the light sources 108A-108D (e.g., LEDs). The apertures 110A-110D in the depicted embodiment may be aligned (e.g., vertically) along a common axis that is parallel with a center axial axis 103A of the test vessel 103.

The lens array 111 that follows the aperture array 110 may be made up of individual lenses 111A-111D that are provided in recessed pockets 112A-112D formed in the first arm 104A adjacent to the aperture array 110. The recessed pockets 112A-112D may be arranged in a relatively precise orientation and the individual lenses 111A-111D may be adhered in the recessed pockets 112A-112D with an optical adhesive or the like. Only one pocket 112A is shown in FIG. 1E, but pockets 112B-112D are identical in structure, except that 112D may be slightly deeper. The individual lenses 111A-111D may have an inner diameter of about 2 mm, and the recessed pockets 112A-112D may have an inner diameter of slightly larger than that, such as about 2.05 mm, for example. Other dimensions may be used. Each lens 111A-111D may include a generally planar surface on the first light receiving surface, and a radiused surface of a light emitting surface thereof. The radius R should be designed to provide a focal length of each lens such that the lens 111A-111D is focused on the center axial axis 103A of the test vessel 103. The lenses 111A-111D may be made of optical quality glass or other low optical loss material. The focal length X3 of each lens should be about 3 mm, for example. Other focal lengths may be used.

In one embodiment, the radius R for the fourth lens 111D may be between about 1.370 mm and 1.380 mm or about 1.375 mm, for example. The fourth lens 111D may be made of ultraviolet-grade fused silica, such as JGS1 fused silica glass available from DayOptics of Fuzhou, China. The other three lenses 111A-111C may have a radius of may be between about 2.545 mm and 2.555 mm, and about 2.550 mm. The other lenses 111A-111C may be made of an N glass material, such as N-LASF9 silica glass available from SCHOTT North America, Inc. of Elmsford, N.Y. The recessed pockets 112A-112D and lenses 111A-111D may be aligned (e.g., vertically) along a common axis that is parallel with a center axial axis 103A of the test vessel 103.

In between the lenses 111A-111D and the aperture array 110 may be a tube array 114 of individual tube sections 114A-114D. Each tube section 114A-114D may have a cylindrical tube configuration having a center axis aligned with a vector of the light signal passing there through. The tube sections 114A-114D may have an inner diameter of about 1.50 mm and a length of about 2.90 mm, for example. Other dimensions and shapes may be used.

To minimize light reflections, the inner walls of the tube sections 114A-114D may include a suitable anti-reflection treatment. The anti-reflection treatment may include perturbations, such as hills 114E and valleys 114F (FIG. 1E) located along at least some of the axial length thereof. In some embodiments, the perturbations may be formed as threads along the inner walls, for example. Other anti-reflection treatments for minimizing light reflections may be used, such as surface roughening, black surface coating, flocking, or the like.

Immediately following the lens array 111, may be a filter array 116. The filter array 116 may be formed of individual filters 116A-116D that may be adhered to the forward end of the recessed pockets 112A-112D adjacent to each lens 111A-111D. Each of the filters 116A-116D may provide band pass filtering of the emitted light signals from the light sources 108A-108D. The filters 116A-116D each may filter at different wavelength bands of light so that the filtered light signals emanating from each towards the test vessel 103 have predefined filtered wavelength bands. For example, the first filter 116A may pass light between 364 nm and 366 nm, the second filter 116B may pass light between 414 nm and 416 nm, the third filter 116C may pass light between 469 nm and 471 nm, and the fourth filter 116D may pass light between 644 nm and 646 nm. The filters 116A-116D of the filter array 116 may be manufactured from a borosilicate float glass material having thin films applied thereon such that each may have a specifically-designed region of transmittance, bounded by defined regions of spectral rejection. The filters 116A-116D may be optical bandpass filters available from Newport Corporation of Irvine, Calif., for example.

Once filtered, the light signals from each filter 116A-116D may pass through a number of corresponding apertures 118A-118D of a second aperture array 118. Each of the apertures 118A-118D of a second aperture array 118 may have a diameter between about 1.20 mm and about 1.80 mm. A nominal diameter of each opening of 1.50 mm may be used. Other diameters may be used. The aperture array 118 may be positioned a distance X4 of about 2.25 mm from the center axial axis 103A of the test vessel 103. Generally though, the diameters of the second apertures 118A-118D may be larger than the first apertures 110A-110D of the first aperture array 110.

Upon exiting the second aperture array 118, the light signals from each aperture 118A-118D sequentially pass through the test vessel 103 including and containing the test sample 105. This exposes the test sample 105 to filtered light signals at four different sequential wavelengths from four different light sources 108A-108D. After passing through the test vessel 103, interfering light signals (i.e., interfering to some extent with the test sample) are received at a single detector 107. The detector 107 may be a single Si PIN photodiode having dimensions of about 2 mm wide by 10 mm high. A model S7509 photodiode from HAMAMATSU of Bridgewater, N.J. may be used. Other sizes and types of photodetectors may be used. However, the detector 107 should have an operational surface large enough to receive light signals from each of the light sources 108A-108D. A long dimension of the detector 107 should be aligned along the center axial axis 103A.

FIG. 2 illustrates a clinical analyzer system 200 utilizing the sample illumination apparatus 102. In operation, at an aspiration station 202, a nozzle 204 that may include a nozzle tip may be positioned by a robot 206 to aspirate a volume of sample fluid from a sample container 208 contained in a sample rack 210. The sample rack 210 may be positioned in a desired and known orientation on a platform or transportation lane 212. The motion (e.g., vertical and/or horizontal) of the nozzle 104 may be controlled by the robot 206 via commands from an aspiration controller 214. Any suitable pump and controls may be used to aspirate the fluid sample. The robot 206 may be provided in any suitable orientation relative to the sample rack 210, such that a sample fluid contained in the sample container 208 may be aspirated and transferred to the test vessel 103 provided in the illumination apparatus 102. It should be understood that one or more reagents may be added to the sample fluid contained in the test vessel 103 from a reagent container (not shown) to form the test sample 105 to be illuminated. However, in some cases, the test sample 105 may simply be plasma or another bodily fluid without reagent for which an absorption reading is desired to be obtained at multiple wavelengths.

The robot 206 may include a frame and a moveable gantry arrangement with the nozzle 204 mounted to a boom, for example. The boom may be moveable (e.g., in the X direction) on a suitable track, slide, worm drive, or guide mechanism by suitable motor. Furthermore, the boom (and the nozzle 204) may be moveable along one or more additional tracks, slides, or guides in an additional direction (e.g., the Y direction). Vertical motion of the nozzle 204 relative to the boom may be accomplished by a vertical motor. The means for moving the robot 206 in the various coordinate directions may include any suitable number of conventional motion-producing mechanisms, such as one or more stepper motors, servo motors, pneumatic or hydraulic motors, electric motors, etc. Furthermore, drive systems including chains, guides, pulleys and belt arrangements, drives such as gear or worm drives, or other conventional drive components may be utilized to cause the motion of the robot 206 and coupled nozzle 204. Other suitable types of robots may be employed.

As shown in FIG. 2, an illumination controller 220 of the apparatus 102 may function to provide control signals to electrical connector 106C so as to cause the light sources 108A-108D to generate light signals at the appropriate times and in the appropriate sequence (to be explained further herein). These light signals emitted from the light sources 108A-108D, are then limited in extent by aperture array 110, focused by lens array 111, filtered by filter array 116, second aperture array 118 and finally passed through the test sample 105 contained in the test vessel 103. The resultant light signals, which may be changed (e.g., diminished due to absorbance or intensified due to luminescence) in intensity due to passing the light signals through the test sample 105 contained in the test vessel 103. The light signals are received as changed light signals at the detector 107.

A method of the invention will now be explained with reference to FIGS. 3-6 herein. The method 500 includes providing an illumination apparatus 102 including a plurality of individually controllable light sources 108A-108D in block 502, and providing a test sample 105 in a test vessel 103 in block 504. The illumination apparatus 102 may be as previously described. The test sample 105 may include blood plasma, blood plasma and a reagent, or another biological fluid, or biological fluid and reagent, for example. The illumination controller 220 of the system 100 may provide signal inputs in input lines 425A-425D to the respective light sources 108A-108D. The signal inputs 425A-425D may bias the light sources ON or OFF. The signal inputs 425A-425D provided to the light sources 108A-108D in block 506 may initially all be constant current signals that bias the light sources 108A-108D to ON (i.e., emitting light signals at their respective center wavelengths). The constant current signals may be provided by constant current sources (not shown) contained in a drive circuit 430. Constant current sources for providing substantially constant electrical current are well known and will not be further described herein. The constant current signals to the light sources 108A-108D are provided for a sufficient time to ensure that any transients have died out and that the intensity of each of the plurality of light sources 108A-108D has become substantially constant. This time may be about 10 microseconds or longer, for example.

The drive circuit 430 and thus the timing and duration of the input signals 425A-425D to the light sources 108A-108D are controlled via a computer 435 operable with a computer interface 440. The computer interface 440 may be a controller area network (CAN) peripheral component interconnect (PCI) interface available from Kvaser Inc. of Mission Viejo, Calif. The computer 435 may be any suitable computer having sufficient memory and processing capability to provide the signal instructions to the drive circuit 430 regarding the desired timing and duration of each of the light sources 108A-108D, and process signals received from the detector 107. The controller 425 may include on-board processor and memory in some embodiments. The controller 425 may include suitable electronics and components to electrically condition, convert, amplify, and/or filter the output signals from the detector 107 in output line 107A, such as the integrate and hold circuit and timing and A/D circuit shown herein.

Figure 6:
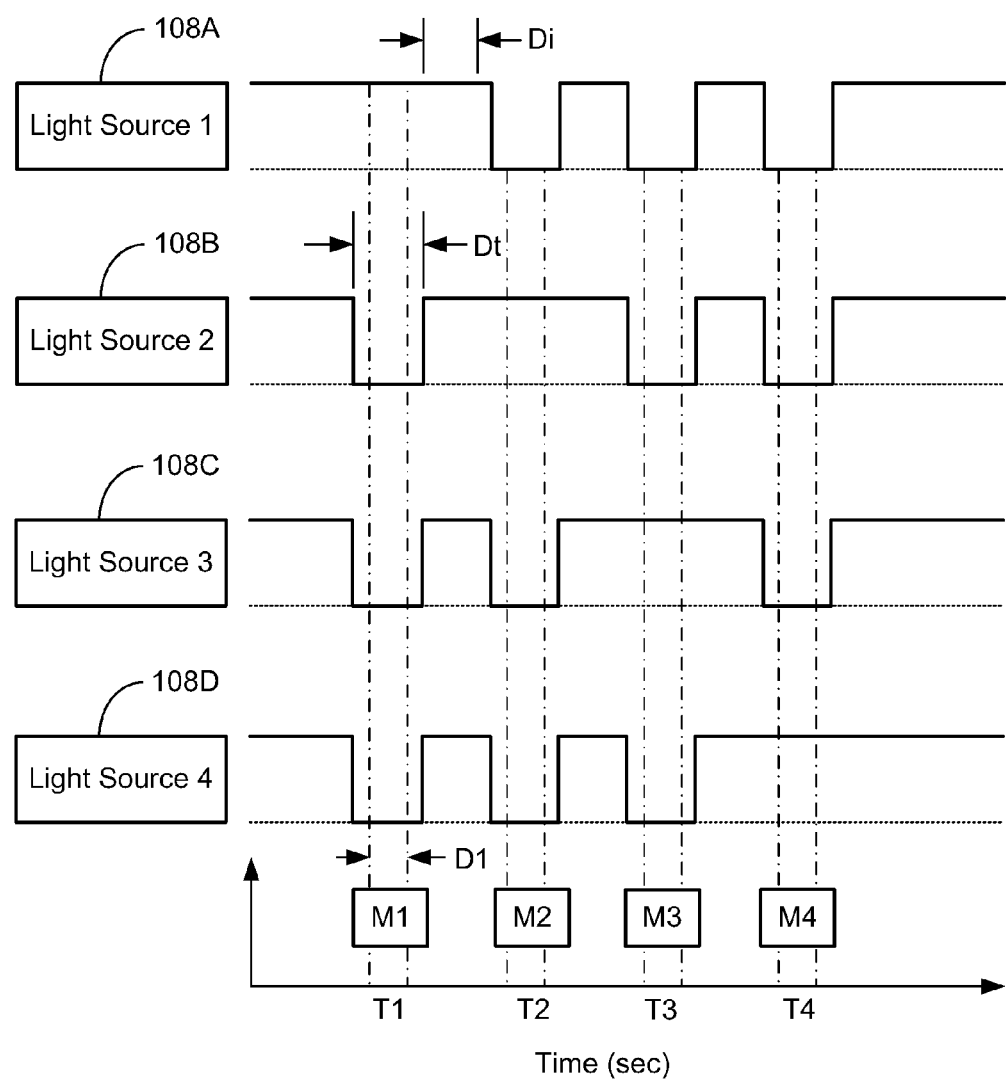
FIG. 6 is a graphical depiction of ON-OFF sequences of the light sources according to embodiments of the present invention.

Once the light sources 108A-108D have equilibrated and are providing substantially constant intensity and wavelength output emissions at their respective center wavelengths, all but a single one of the light sources 108A-108D are turned OFF for a short duration Dt (e.g., between about 50 and 500 microseconds, and in some embodiments about 100 microseconds) in block 508. For example, as shown in FIG. 6, light sources 108B-108D are turned off for a short duration Dt such that a reading may be taken during time T1. Time T1 is a short time sub-segment of the duration D1 during which an integration is done. At the end of D1, the integrated signal is held. The detected held voltage at the detector 107 is measured during duration Di. Di may be about 10 mill seconds, for example. During readings of the test sample 105, the signal received at the detector 107 in block 510 is a changed light signal. The detector 107 may be a single photodetector. The light emitted at the first wavelength from the first light source 108A is changed as the light signal passes through the test sample 105 contained in the test vessel 103. In one embodiment, an extent that the light signal is changed may be correlatable to the absorbance through the test sample 105. Successive readings may be taken at times T2, T3, and T4 at the other center wavelengths of interest. In each case, all but the single light source of interest (having a predefined center wavelength) is turned off for a short duration Dt in block 512.

This is repeated until readings are obtained at every center wavelength of interest, such as the four described above. In block 514, the extent of signal change may be determined by comparison to a baseline reading as discussed below. This signal change at each wavelength may be used to determine an absorbance at each respective wavelength of interest. This data may be correlated to the presence and concentration of an analyte in the test sample 105, for example.

Prior to or after taking the sequence of readings at the plurality of wavelengths, a baseline reading at T1, T2, T3, and T4 may be established for each light source 108A-108D in a manner as described above, but without any test sample 105 being contained in the test vessel 103. This may be done before or after each new illumination test of a test sample 105 or before or after every few test sample illumination tests. Other intervals may be used for obtaining the baseline readings. Accordingly, the invention provided an extent of light signal change at each center wavelength. As should be recognized, advantageously, the present method and apparatus accomplish testing without a reference sensor as required in the prior art. Because the light sources are only turned OFF for a very brief period of time, the light sources remain very constant in temperature, and, thus, emit relatively constant wavelengths and intensity of light emission.

In an alternative embodiment, each of the light sources 108A-108D may be pulsed at a relatively high frequency (e.g., about 15,000 cycles/sec) in the pattern described above, (i.e., with only one source on at a time during individual readings). The duration would be much shorter (e.g., about 33 microseconds) and the successive readings for each cycle may be averaged to arrive at an intensity reading to compare against the baseline.

Figure 7:
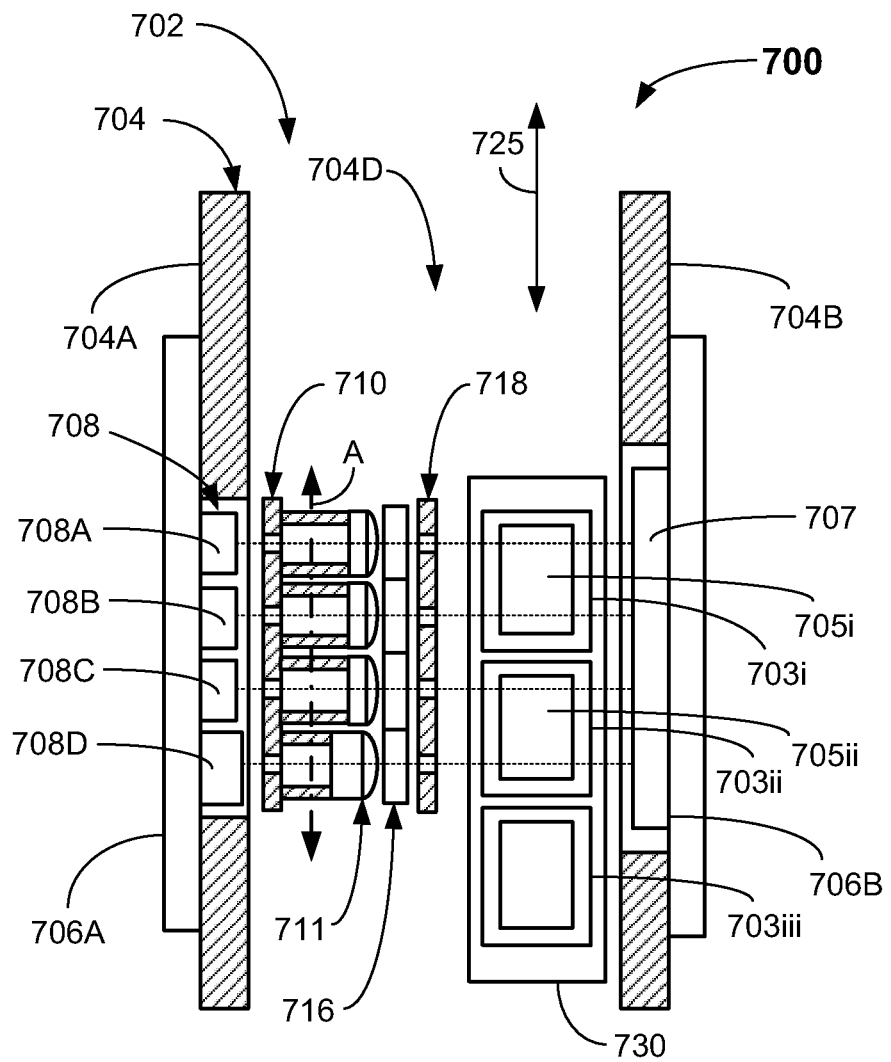
FIG. 7 is an isometric view illustration of an exemplary illumination apparatus according to embodiments of the invention.

In yet another embodiment, as shown in FIG. 7, an illumination system 700 is shown. In this embodiment, a train or line of test vessels 703$i$-703$iii$, at least some of which containing a test sample 105, are provided and moved one by one in front of an illumination apparatus 702. The illumination apparatus 702 may include a bracket 704 including spaced apart arms 704A, 704B and a space 704D between them as previously described. Furthermore, the illumination apparatus 702 may include a light source array 708 including a plurality of light sources 708A-708D, one or more aperture arrays 710, 718, a lens array 711, a filter array 716, and a single detector 707 as previously described. The light source array and detector may be mounted on, or electrically coupled to, circuit boards 706A, 706B as previously described. In this embodiment, however, the central axis of each test vessel 703$i$-703$iii$ may be oriented perpendicularly to an axis "A" of the aligned lenses of the lens array 711 and light sources 708A-708D of the array of light sources 708. In other words, the center axis of the test vessel is into and out of the paper as shown.

In operation, a first test vessel 703$i$ may be positioned at a first location (e.g., in front of light sources 708A, 708B), while a second test vessel 703$ii$ may be positioned at a second location (e.g., in front of light sources 708C, 708D). A third test vessel 703$iii$ may be positioned at a third location in the train adjacent to the second location. All may be moveable in either direction indicated by arrow 725 so that the test vessels may reside in front of any one or more than one of the light sources 708A-708D. A transport device 730 may be provided and adapted to move the plurality of test vessels 705$i$, 705$ii$, 705$iii$ into alignment with at least some light sources of the array of light sources 708. As discussed before, all sources 708A-708D may be illuminated initially. Then readings may be taken through the various test samples 705$i$, 705$ii$.

For example, test sample 705$i$ may receive at the detector 707, changed light signals at the first and second wavelengths of the first and second light sources 708A, 708B via shutting off sequentially all but 708A and 708B, one after the other. Likewise, readings may be taken through test sample 705$ii$ and received at the detector 707 at the third and fourth wavelengths via shutting off sequentially all but light sources 708C, 708D, one after the other. The train may then be moved by the transport device 730. The transport device 730 may be a moveable conveyor, moveable cassette tray, or moveable sample rack, robot platform or the like such that readings at the other two wavelengths may be taken on test sample 705$i$ and 705$ii$. For example, readings on test sample 705$i$ may have been taken first in the position that test sample 705$ii$ is depicted in, then the test sample 705$ii$ may be moved to the position shown occupied by 705$i$ and readings at the other two wavelengths may be taken. Thus, it should be apparent that two readings may be taken at each station/location.

If the illumination apparatus may be made compact enough, then each of the train of test vessels may be stopped at one location only where all four wavelength readings may be obtained. Optionally, the light source array 708, lens array 711, filter array 716, and one or more aperture arrays 710, 718 may be rotated 90 degrees from the orientation shown, such that the axis A will be substantially aligned with an center axial axis of each test vessel (e.g., with test vessel 705$i$). Thus, in this orientation, all four readings may be taken on each vessel during one stop.

In accordance with another aspect, test vessel 703$iii$ may be empty and used to perform a baseline test. For example, a baseline test may be run every other sample, or for every other few samples that are tested. Empty vessels such as 703$iii$ may be positioned at any suitable location in the train and baseline tests may be performed at whatever intervals that are desired.

While the invention is susceptible to various modifications and alternative forms, specific system and apparatus embodiments and methods thereof have been shown by way of example in the drawings and are described in detail herein. It should be understood, however, that it is not intended to limit the invention to the particular systems, apparatus, or methods disclosed but, to the contrary, the intention is to cover all modifications, equivalents, and alternatives falling within the spirit and scope of the invention.

What is claimed is:

1. A method of illuminating a test sample, comprising:
providing an illumination apparatus having a plurality of controllable light sources, each having an emission wavelength;
providing a test vessel containing the test sample;
providing a constant current to turn on each of the plurality of controllable light sources at the same time until each of the plurality of controllable light sources provides substantially constant intensity;
turning off all but a single one of the plurality of controllable light sources;
receiving a changed light signal at a single detector from the single one light source passed through the test sample; and
repeatedly turning off all but a single other light source until readings at all wavelengths of interest are obtained.

2. The method of illuminating of claim 1, wherein the plurality of light sources emits light signals at four different wavelengths having center wavelengths between:
355 nm and 375 nm,
405 nm and 425 nm,
460 nm and 480 nm, and
635 nm and 655 nm.

3. The method of illuminating of claim 2, further comprising passing each of the light signals through a corresponding first aperture having a diameter between about 0.35 mm and about 0.60 mm.

4. The method of illuminating of claim 2, further comprising filtering each of the four different wavelengths of light so that filtered light signals have filtered wavelength bands between:
364 nm and 366 nm,
414 nm and 416 nm,
469 nm and 471 nm, and
644 nm and 646 nm.

5. The method of illuminating of claim 2, further comprising passing each of the plurality of light signals through a corresponding lens and then through a corresponding second aperture having a diameter between about 1.20 mm and about 1.80 mm.

6. The method of illuminating of claim 2, further comprising passing the light signal having a center wavelength between 355 nm and 375 nm through a lens having a radius of between about 1.370 mm and about 1.380 mm.

7. The method of illuminating of claim 2, further comprising passing each of the light signals from the other three wavelengths through lenses each having a radius of between about 2.545 mm and about 2.555 mm.

8. An illumination apparatus, comprising:
a bracket including a first arm and a second arm and a space between the arms adapted to receive a test vessel;
an array of light sources coupled to the first arm, each light source having an emission wavelength;
a lens array coupled to the first arm, a lens aligned with each light source in the array of light sources in a direction of light signal travel towards the space;
an array of optical bandpass filters, an optical bandpass filter aligned with each light source;
at least one aperture array;
a single photo detector coupled to the second arm; and
a controller operable to:
provide a constant current to turn on each of the light sources at the same time;
turn off all but a single one of the light sources;
receive a changed light signal at the single detector from the single one light source passed through the test vessel; and
repeatedly turn off all but a single other light source until readings at all wavelengths of interest are obtained.

9. The apparatus of claim 8, wherein the array of light sources comprise light emitting diodes aligned along a central axis of the test vessel.

10. The apparatus of claim 8, wherein the array of light sources comprise four different light sources adapted to emit four different wavelengths of light having center wavelengths between:
355 nm and 375 nm,
405 nm and 425 nm,
460 nm and 480 nm, and
635 nm and 655 nm.

11. The apparatus of claim 10, wherein the array of bandpass filters comprise filtered wavelength bands between:
364 nm and 366 nm,
414 nm and 416 nm,
469 nm and 471 nm, and
644 nm and 646 nm.

12. The apparatus of claim 10, wherein at least two of the array of lenses comprise different radius curvatures.

13. The apparatus of claim 8, comprising a light tube immediately prior to each lens, the light tube including a wall having an anti-reflective surface treatment.

14. The apparatus of claim 13, wherein the light tube comprises threads on the wall.

15. The apparatus of claim 8, comprising a light conditioning assembly including:
the array of lenses, each lens including an outer diameter received in a recessed pocket, a planar entry surface, and a curved emitting surface;
an array of light tubes adapted to channel light to the planar entry surfaces of the array of lenses; and
a first array of apertures adapted to limit an extent of light entering each of the light tubes.

16. The apparatus of claim 15, comprising a second array of apertures between the array of lenses and the space between the arms adapted to receive a test vessel.

17. The apparatus of claim 8, comprising a transport device adapted to move a plurality of test vessels into alignment with at least some light sources of the array of light sources.

18. An illumination system, comprising:
a bracket including a first arm and a second arm and a space between the arms;
a test vessel provided in the space;
an array of light sources operable to provide light signals through the test vessel;
an array of lenses, a lens corresponding to each light source;
an array of bandpass filters adapted to filter the light signals from the array of light sources, a filter corresponding to each light source;
at least one aperture array;
a single detector adapted to receive changed light signals passing through the test vessel; and
a controller operable to control a sequence of light signals emitted from the array of light sources by:
providing a constant current to turn on each of the light sources at the same time;
turning off all but a single one of the light sources;
receiving a changed light signal at the single detector from the array of light sources passed through the test vessel; and
repeatedly turning off all but a single other light source until readings at all wavelengths of interest are obtained.

19. The illumination system of claim 18 wherein the array of light sources are substantially aligned along a center axial axis of the test vessel.

20. The illumination system of claim 18 wherein the at least one aperture array comprises a first aperture array located between the array of light sources and the array of lenses and a second aperture array located between the array of lenses and the test vessel.

* * * * *